United States Patent [19]

Free et al.

[11] Patent Number: 5,000,737
[45] Date of Patent: Mar. 19, 1991

[54] SINGLE USE DISPOSABLE SYRINGE

[75] Inventors: Michael J. Free; Terence R. Ellard, both of Seattle, Wash.

[73] Assignee: Program for Appropriate Technology in Health (PATH), Seattle, Wash.

[21] Appl. No.: 559,394

[22] Filed: Jul. 26, 1990

Related U.S. Application Data

[63] Continuation of Ser. No. 370,742, filed as PCT US87/02408 on Sept. 18, 1987, abandoned.

[51] Int. Cl.⁵ ............................................... A61M 5/00
[52] U.S. Cl. .................................... 604/110; 604/218; 604/220
[58] Field of Search ............... 604/110, 128, 181, 187, 604/218, 220–222, 228, 229, 234, 241; 222/389, 391

[56] References Cited

U.S. PATENT DOCUMENTS

| | | | |
|---|---|---|---|
| 1,496,654 | 2/1924 | Crowther | 604/220 |
| 2,216,354 | 10/1940 | Pletcher | 604/220 |
| 2,618,263 | 11/1952 | Lakso et al. | 604/192 |
| 3,890,971 | 6/1975 | Leeson et al. | 604/220 |
| 4,013,073 | 3/1977 | Cunningham | 604/204 |
| 4,022,206 | 5/1977 | Hilleman et al. | 604/197 |
| 4,270,536 | 6/1981 | Lemelson | 604/110 |
| 4,367,738 | 1/1983 | Legendre et al. | 604/187 |
| 4,386,606 | 6/1983 | Tretinyak et al. | 604/220 |
| 4,391,273 | 7/1983 | Chiquiar-Arias | 604/110 |
| 4,548,601 | 10/1985 | Lary | 604/204 |
| 4,713,056 | 12/1987 | Butterfield | 604/110 |
| 4,731,068 | 3/1988 | Hesse | 604/110 |
| 4,758,232 | 7/1988 | Chak | 604/220 |
| 4,781,683 | 11/1988 | Wozniak et al. | 604/236 |
| 4,781,684 | 11/1988 | Trenner | 604/218 |
| 4,840,616 | 6/1989 | Banks | 604/218 |

FOREIGN PATENT DOCUMENTS

| | | |
|---|---|---|
| 16543/88 | 5/1988 | Australia . |
| 1070785 | 12/1959 | Fed. Rep. of Germany . |
| 3107414A1 | 9/1982 | Fed. Rep. of Germany . |
| 1257067 | 2/1960 | France . |
| 2319383 | 7/1976 | France . |
| 0291109 | 4/1988 | Netherlands . |
| 2205750A | 12/1988 | United Kingdom . |

Primary Examiner—Stephen C. Pellegrino
Assistant Examiner—Michael Rafa
Attorney, Agent, or Firm—Seed and Berry

[57] ABSTRACT

A single use syringe including a mechanical means permitting a single withdrawal of the plunger to load the cylinder an a single advance of the plunger to inject the material, thereafter incapacitating the mechanism. The mechanical means may well be retrofit to existing syringes.

15 Claims, 4 Drawing Sheets

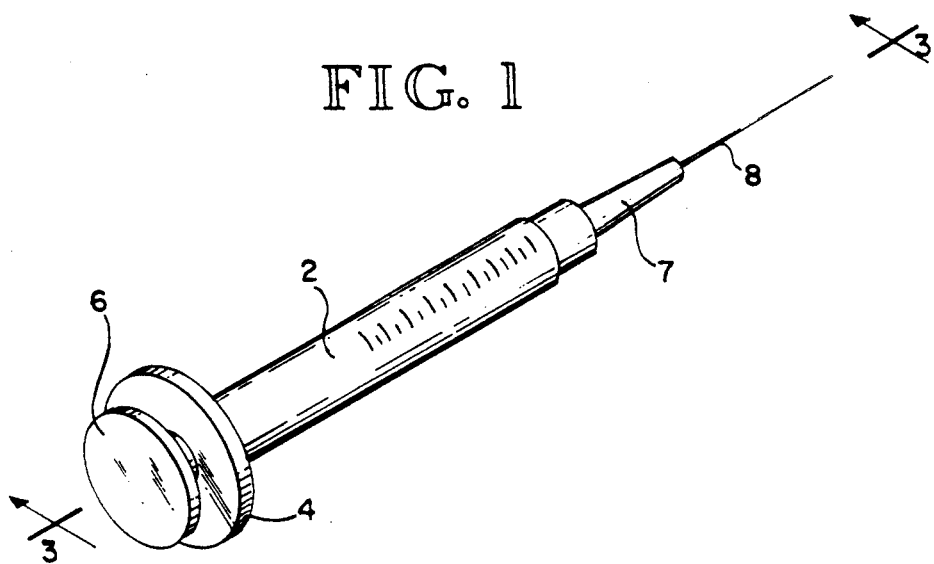
FIG. 1
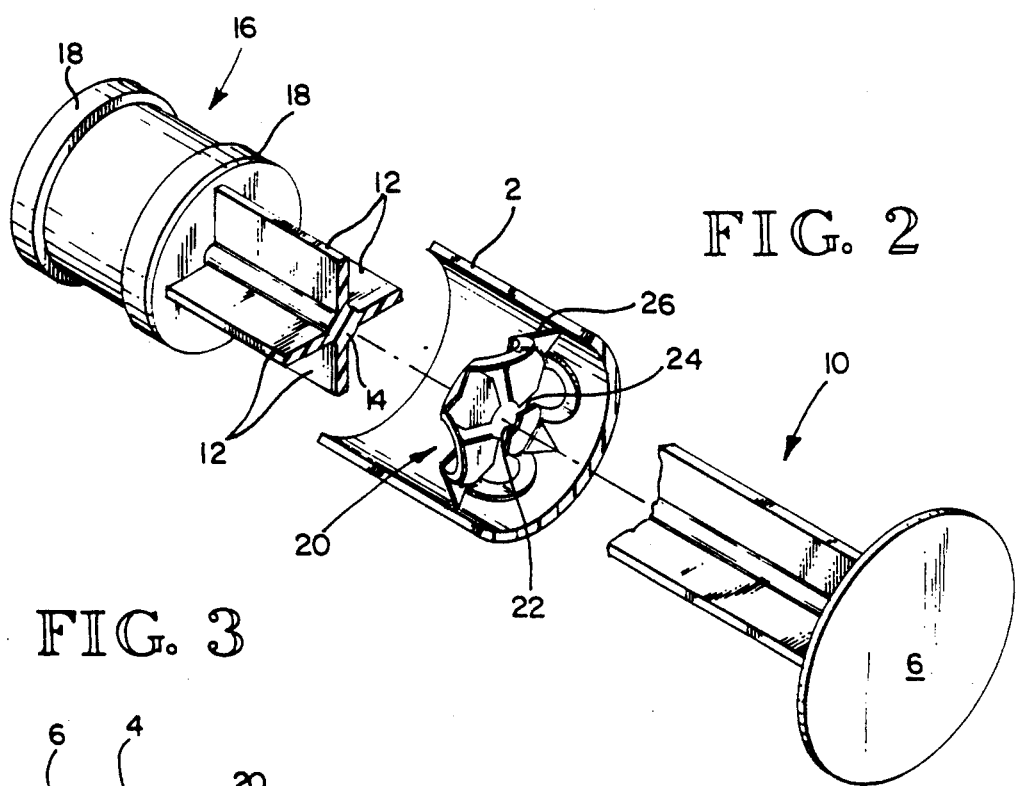
FIG. 2
FIG. 3
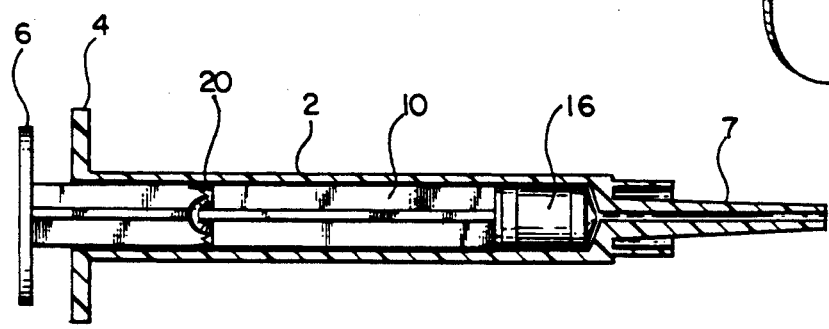

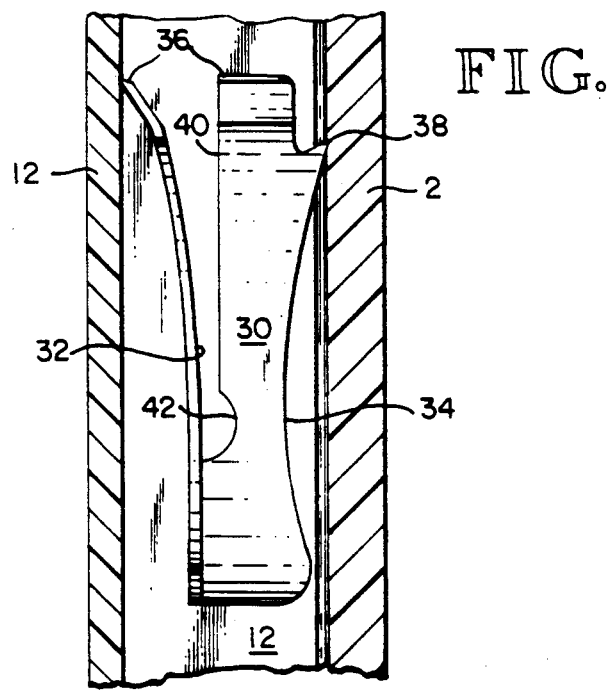
FIG. 8
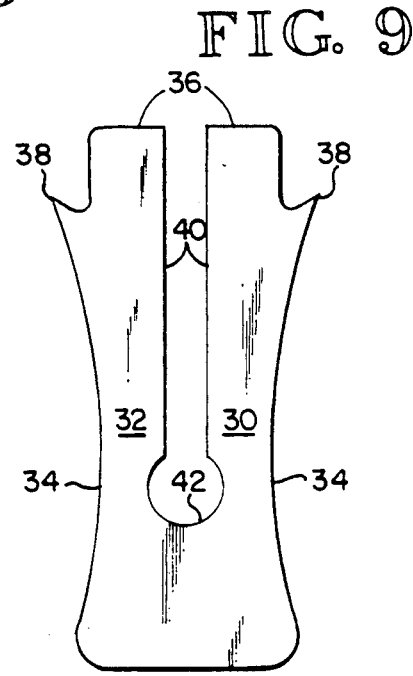
FIG. 9
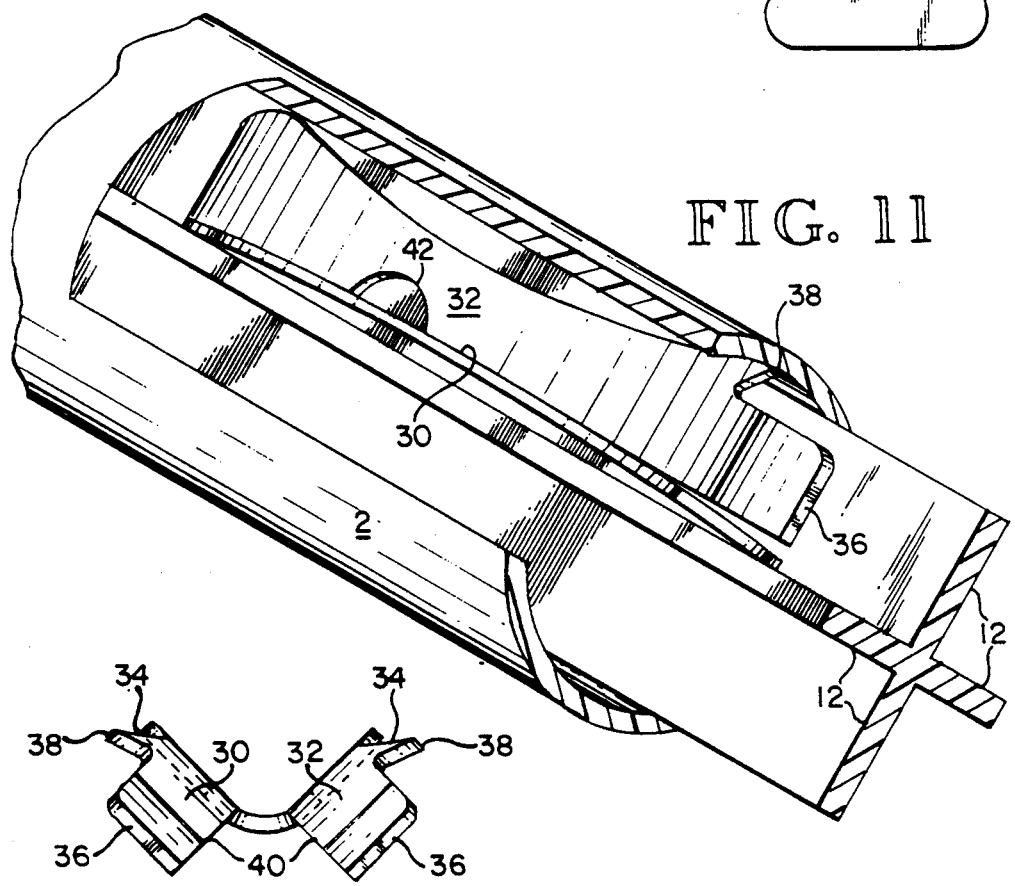
FIG. 11
FIG. 10

SINGLE USE DISPOSABLE SYRINGE

CROSS-REFERENCE TO RELATED APPLICATION

This application is a continuation of U.S. application Ser. No. 07/370,742 filed as PCT US87/02408 on Sept. 18, 1987, now abandoned.

DESCRIPTION

1. Technical Field

This invention relates to a single use disposable syringe, and more particularly, to an essentially rigid syringe having a fixed needle wherein the syringe is rendered unusable by including a hard flute or disc which through interaction of relative moving parts only permits a single cycle of the plunger before locking it in position.

2. Background Art

Standard disposable syringes, although intended for one time use, are constructed in such a way that they can be re-used. Proper one-time use, destruction and disposal of these devices requires strict compliance on the part of the user, generally in a controlled environment.

In an environment which does not include appropriate controls, i.e. outside of a hospital or clinic, disposable syringes have gotten into the hands of people who have used them improperly; e.g. employing them for injections of illegal drugs, or injection into two or more persons, without adequate sterilization between uses.

In addition to the diversion of used disposable syringes from legitimate sources for administration of illegal and dangerous drugs, the syringes, when not properly sterilized, become a vehicle for the transmission of diseases including the HIV virus (AIDS) and hepatitis B.

One of the methods proposed to prevent the reuse of syringes has been to package the medication in a single dose self-destructive collapsible container which is then squeezed and collapsed to administer the medication.

However, not all medications are suitable for use in prefilled single dose systems. Some medications are most economically and desirably distributed in a multi-dose container. These can then be administered with a single use, disposable syringe, or a multiple use sterilizable syringe.

Prior art devices which have dealt with the problem of reusable syringes in one form or another include U.S. Pat. No. 2,618,263 granted to Lakso et al Nov. 18, 1952 which discloses a premeasured medication in an ampule adjacent to the inner end of a needle. Upon pressure being applied to the ampule, the needle penetrates the ampule and the medication is discharged. The entire device is then disposed.

U.S. Pat. No. 4,013,073 granted to Cunningham on Mar. 22, 1977 discloses a collapsible single use syringe wherein the interior of the collapsible wall is constructed such that when the walls are pressed together to discharge the medication they interlock and therefore render the device impossible to reuse.

U.S. Pat. No. 4,022,206 granted to Hilleman et al May 10, 1977 discloses a method and apparatus for storing and delivering a lyophilized vaccine in a single dose prepackaged system but makes no provision for rendering the unit not reusable.

U.S. Pat. No. 4,391,273 granted to Chiquiar-Arias July 5, 1983 discloses a rigid type syringe including a pin which is attached to the piston and which penetrates the bottom wall of the cylinder when the injection has been completed. In the alternative, this patent discloses a knife which permits movement of the cylinder in a forward direction but cuts the sidewall of the cylinder if there is an attempt to recycle the piston or reuse the syringe.

U.S. Pat. No. 4,548,601 granted to Larry on Oct. 22, 1985 discloses a prepackaged pharmaceutical including an inner and outer flexible envelope such that the inner envelope will remain collapsed due to atmospheric pressure once the injection is completed.

SUMMARY OF THE INVENTION

The present invention lies in a single use syringe wherein reuse is mechanically prohibited.

It is an object of the present invention to provide a single use syringe which is simple of construction, inexpensive and automatically prevents reuse.

Another object of this invention is to provide an inexpensive flute or disc which when placed upon the plunger shaft of a standard plastic disposable syringe will allow a single reverse movement to load the syringe and a single forward motion to administer the medication but will then lock the plunger in position to prevent further use.

It is another object of the present invention to provide an inexpensive means for rendering a syringe non-functional following the initial administration.

Another, object of this invention is to provide a means whereby syringes of identical capacity can be restricted to contain and deliver different fractional volumes, thereby reducing the need for syringes of different sizes.

BRIEF DESCRIPTION OF THE DRAWINGS

FIG. 1 is a pictorial representation of a typical syringe which would utilize the present invention.

FIG. 2 is an isometric view of the plunger/cylinder assembly with the inventive single use disc in position.

FIG. 3 is a sectional view along lines 3—3 of FIG. 1 depicting the disc in position prior to use of the syringe.

FIG. 8 is a view of a second embodiment of the present invention in the form of a flute in place within the syringe.

FIG. 9 is a vertical view of the inventive flute outside the syringe.

FIG. 10 is a bottom plan view of the inventive flute of FIG. 8.

FIG. 11 is an isometric of the inventive flute of FIGS. 8-10 in operative position.

BEST MODE FOR CARRYING OUT THE INVENTION

Figure 4:
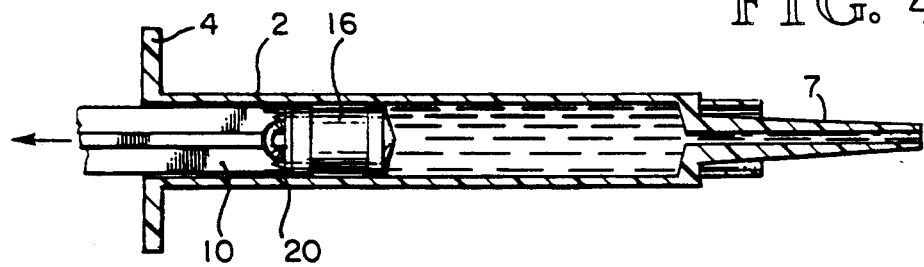
FIG. 4 is similar to FIG. 3 showing the syringe with the measuring tube filled with medicine.

As seen in FIG. 1, the environment of the present invention is a rigid plastic syringe having a main cylinder 2, an outwardly extending upper disc portion 4 for ease in administering the medication, a cap 6 which is the terminus of the outer end of the plunger as described hereinafter and an administering element 8 protruding from nose 7.

Referring now to FIG. 2, the cap member 6 as seen in the lower end of this figure is connected to or integral with plunger member 10. Plunger member 10 is generally of X configuration in cross-section having legs 12 and a central interconnecting cylindrical member 14. Piston member 16, including sealing elements 18, completes the plunger element at the opposite end to cap 6. Approximately midway of the plunger member, in this figure, there is depicted a portion of the cylinder 2 and the inventive disc 20. As will be described in greater detail hereinafter, the inventive disc 20 includes a central opening 22 to receive the cylindrical portion 14, radial slots 24 to receive legs 12, an outwardly projecting points or darts 26. It is to be understood that the internal elements 22, 24 which are in contact with the plunger shaft 10 are biased, as better seen in FIG. 6, such that movement relative to the two contiguous elements in one direction is substantially without resistance whereas movement in the opposite direction causes the disc element 20 to embed itself in the shaft. Likewise, the outwardly projecting darts or arrows 26 will readily move in one direction along the inside wall of cylinder 2 but any attempt at relative movement in the opposite direction will cause the darts 26 to impinge in the inner wall of cylinder 2.

It is to be understood that the most consistent operation will be generated by utilizing a material for the disc, such as stainless steel which has memory and is hard, while utilizing a plastic material for the syringe itself. The relative hardness between the two materials permits the configured disc 20 to react against relative movement of contiguous elements, impinging itself into the softer material, and preventing further movement.

Referring now to FIG. 3, the device is shown in cross-section without the needle in a configuration wherein the syringe is empty and ready for use. It is to be noted that the piston member 16 is adjacent the nose 7 and the configured disc 20 is located a predetermined distance to the rear of the cavity such that a withdrawal of the cylinder to this point will draw a predetermined amount of medication into the cylinder for administration. The ring is prevented from moving rearwardly because the darts 26 are locked to the inner wall of the cylinder. The plunger, however, is free to move in this direction.

It is to be noted that the inventive device could readily be used, depending upon initial placement, to control the syringe volume.

FIG. 4 depicts the inventive syringe with the piston member 16 withdrawn to a position adjacent the disc 20, the cylinder being filled with the medication and the cylinder prevented from further rearward movement by the disc 20 and its points which impinge themself on the inner wall of the cylinder 2.

Figure 5:
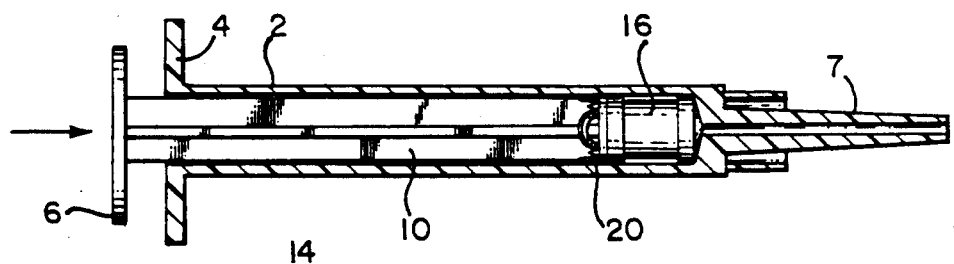
FIG. 5 is a depiction similar to that of FIG. 3 showing the apparatus following the administration of the medication and with the cylinder locked against the end of the measuring tube.

As seen in FIG. 5, the medication has been applied, the forward movement of plunger 10 has carried the disc 20 to its forwardmost position locking the piston 16 against the front of the cylinder 2. The disc was moved forward through coaction with the plunger. An attempted rearward movement of the plunger will again cause the points on the plate to impinge in the inner wall of the cylinder 2 preventing further reverse movement.

Figure 6:
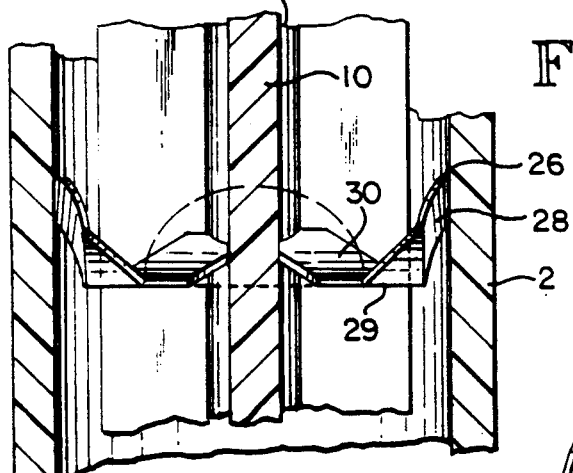
FIG. 6 is a sectional view through the plunger and disc depicting the interaction of the various elements.

Reference is now made to FIG. 6 wherein the inventive disc is shown in position secured between the inner side wall of the syringe cylinder 2 and the X shaped plunger shaft having legs 10 and a central cylindrical portion 14. As easily seen in this figure, the upwardly projected darts or arrows 26 which are the terminus of upwardly facing flat portions 28 meet in a bend line 29 the opposite side of which forms the upwardly projecting body elements 30 which contact the plunger member.

Figure 7:
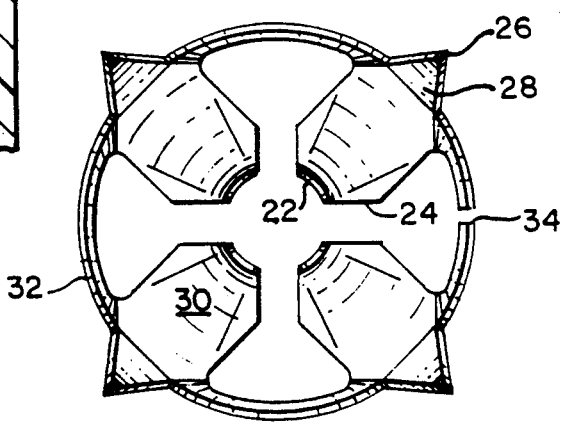
FIG. 7 is a plan view of the inventive disc including an alternate configuration.

Referring now to FIG. 7, the inventive disc may be seen in plane view and is to be noted that the point elements 26, 28 are joined by arcuate elements 32 to reduce the weight and increase the flexibility of the ring. As seen to the right of FIG. 7, a slot 34 may be placed in arc 32 to facilitate assembly of the ring onto the plunger.

FIGS. 8, 9, 10 and 11 depict an alternate embodiment of the invention employing a hard flute instead of a disc. This embodiment allows for easy assembly into standard disposable syringes either at the time of manufacture or later, and will accomplish the purpose of allowing the plunger to be retracted to draw the fluid into the syringe up to a predetermined volume and then allow the plunger to expel the fluid and will also prevent a second retraction.

FIG. 9 shows the second embodiment in plan view in the form of a thin metal flute including legs 30, 32 having a slight waist portion 34. At the upper portion, the legs are separated by a slot 40 terminating in the lower portion with a stress reducing arcuate portion 42.

FIG. 10 shows the flute in end view in which legs 30 and 32 can be seen to be disposed at right angles to each other, flared outwardly and sharpened at the upper end including a chisel portion 36 and a pointed dog 38.

As is apparent from viewing FIGS. 8 and 11, the restrictive flute is placed in position between the interior sidewall of the cylindrical portion of the syringe 2 and the legs 12 of the plunger such that a chisel portion 36 will dig into the plunger legs 12 when there is relative movement therebetween in one direction whereas relative movement in the other direction is substantially without resistance. The spur 38 will impinge itself in the side wall of the cylinder 2 when there is relative movement therebetween in one direction whereas relative movement in the other direction is substantially without resistance. The plunger can thus be withdrawn, drawing fluid into the cylinder until the piston 16 in FIG. 2 is prevented from further outward movement by the flute impinged in the side wall of the cylinder 2. During the injection process, the chisel portion of the flute 36 will impinge on the legs 12 of the plunger and will be moved downwardly with the plunger shaft until the fluid is ejected. The flute then prevents rearward movement of the plunger by means of the spur 38 which will again embed into the sidewall of the cylinder 2.

Figure 12:
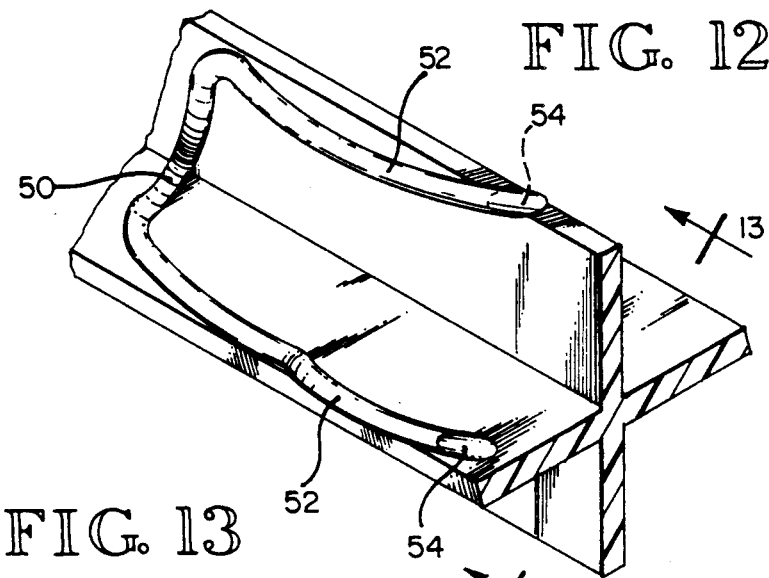
FIG. 12 is a representation of a wire device for accomplishing the purposes of the present invention as shown in conjunction with the plunger body.
Figure 13:
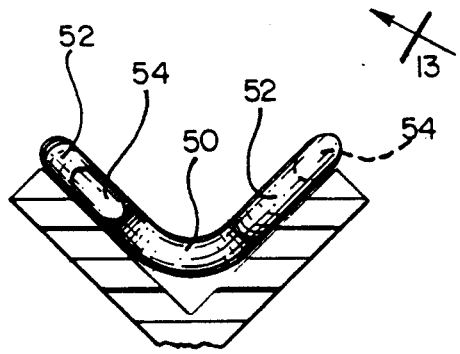
FIG. 13 is a view along lines 13—13 of FIG. 12.
Figure 14:
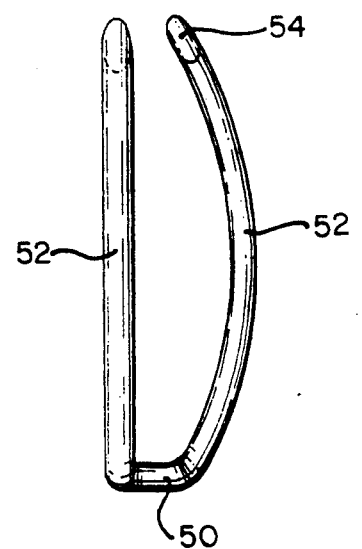
FIG. 14 is a side elevation view of the device of FIG. 12.

Referring now to FIG. 12, yet another embodiment of the present invention can be seen. This embodiment comprises a wire form which is generally in the shape of a distorted U-configuration having a base member 50 which is bent to generally conform to the V-formed in the sidewall of the plunger and a pair of upwardly and outwardly flared arm members 52 each of which is sharpened to a chisel-type point 54 such that when placed in position between the interior sidewall of the cylinder and the plunger for the piston it acts similarly to the restrictive flute device as described with respect to FIGS. 8-11.

Figure 15:
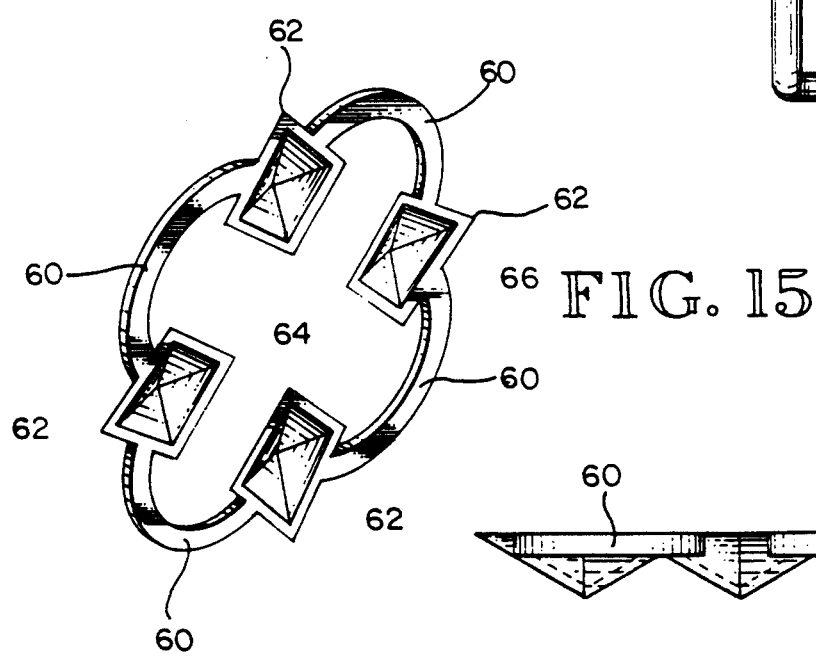
FIG. 15 is a pictorial representation of yet another device meeting the object of the present invention.
Figure 16:
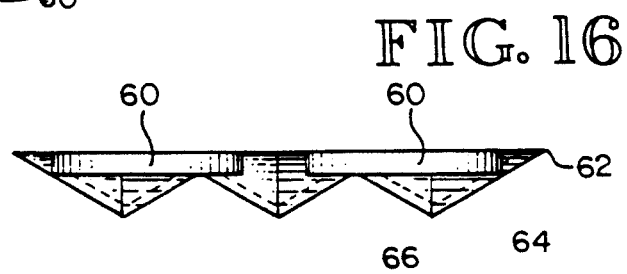
FIG. 16 is a side elevation view of the device of FIG. 15.

Reference is now had to FIGS. 15 and 16 wherein there is depicted yet another embodiment of the present invention which would preferably be fabricated of a plastic material which would be harder than the plastic of which the syringe is fabricated. In general, this restrictive device will be used in a similar manner to those described hereinabove and it is fabricated of a cloverleaf configuration wherein the arcs of the clover leaves are thin flexible bands 60 which are joined at their intersecting cusps by diamond-shaped engaging members 62 including integral reinforcing projections 64 each having four triangular sidewalls 66. The diamond element 62 resists any bending moment which will occur during attempted relative movement of the plunger with respect to the sidewall causing the points of the diamond 62 to dig into the interior wall of the cylinder and/or the plunger respectively.

Thus as can be seen, the present invention contemplates an inexpensive method of changing a standard disposable syringe to one that is only useable syringe of a given size to be used restrictively to administer differing volumes of medication by varying the placement of the device.

We claim:

1. A single use syringe comprising:
    an elongated hollow cylindrical barrel having an interior sidewall, a proximal end, a distal end, and a nozzle closing said distal end of said barrel;
    a plunger member within said barrel for axial movement therein for drawing fluid into and expelling fluid out of said barrel through said nozzle, said beyond said barrel at said proximal end and having a piston at the distal end;
    a control device placed at a predetermined position within the barrel between the plunger shaft and the interior wall, which position determines the volume of the syringe to be filled with medication, the control device being elongate and including a distal portion and proximal portion, the proximal portion of the control device having
    (a) a proximally oriented outwardly facing element of a material harder than the interior sidewall and contacting and angled against the interior sidewall so that the control device is free to move toward the distal end but proximal movement of the plunger shaft after the piston contacts the distal portion of the control device causes the outwardly facing element to embed into the interior sidewall preventing further proximal movement of the piston and said control device, and
    (b) a proximally oriented inwardly facing element contacting and biased against the plunger shaft so that the plunger shaft is free to move first time toward the proximal end but distal movement of the plunger shaft causes the inwardly facing element to engage the plunger shaft so that the control device moves with the plunger shaft toward the distal end,
    whereby the control device permits the syringe to be loaded with medication in the volume defined by the predetermined position of the control device by proximal movement of the piston as far as the distal end of the control device; and after suppression of the plunger shaft to expel the medication, any second proximal movement of the plunger shaft is prevented by the outwardly facing element embedding into the interior sidewall.

2. The syringe of claim 1 wherein said plunger shaft includes longitudinally oriented planar legs having surfaces for engaging said inwardly facing element.

3. The syringe of claim 1 wherein said control device includes a second proximally oriented, outwardly facing element and a second proximally oriented, inwardly facing element.

4. The syringe assembly of claim 3 wherein said inwardly facing element and said second inwardly facing element are separated by a longitudinally slot in said element so that said inwardly facing element and said second inwardly facing element extend proximally in cantilever spring-like fashion from said distal portion of said device forming said outwardly facing element and said second outwardly facing element against said interior side wall of said barrel.

5. The syringe of claim 3 wherein said plunger shaft includes at least two longitudinally oriented planar legs having surfaces for engaging said inwardly facing element and said second inwardly facing element said legs being positioned so that said inwardly facing element and said second inwardly facing element engage different planar legs.

6. The syringe of claim 5 wherein at least two of said planar legs are oriented substantially perpendicularly with respect to each other forming a V-shaped axial groove along the length of said plunger shaft for engaging said control device.

7. The syringe of claim 1 wherein said barrel is made of plastic material.

8. The syringe of claim 1 wherein said control device is made of metal.

9. The syringe of claim 1 wherein said control device is made of sheet metal.

10. The syringe of claim 9 wherein said sheet metal is stainless steel.

11. A device for use in conjunction with a plastic syringe having an elongated hollow cylindrical barrel with an interior sidewall, a proximal end, a distal end, and a nozzle closing said distal end of said barrel; a piston within said barrel and a plunger shaft connected to said piston extending beyond said barrel at the proximal end, to allow selective adjustment of the volume, comprising:
    an elongate flute placed within the barrel between the plunger shaft and the sidewall of the plastic syringe, for preventing retraction of the piston beyond the flute whereby appropriate placement of the flute determines the volume of the syringe, said flute fabricated of a material harder than the material of the syringe.

12. A device for use in conjunction with a plastic syringe having an elongated hollow cylindrical barrel with an interior sidewall, a proximal end, a distal end, and a nozzle closing said distal end of said barrel; a piston within said barrel and a plunger shaft connected to said piston extending beyond the said barrel at the proximal end, to allow selective adjustment of the volume, comprising:
    a bent wire placed within the barrel between the plunger shaft and the sidewall of the plastic syringe for preventing retraction of the plunger beyond the bent wire whereby appropriate placement of the bent wire determines the volume of the syringe, said bent wire being fabricated of a material harder than the material of the syringe.

13. The syringe of claim 1 wherein the outwardly facing element of the control device terminates in a spur contacting and angled against the interior sidewall and the inwardly facing element of the control device terminates in a chisel portion contacting and biased against the plunger shaft.

14. The syringe of claim 1 wherein said plunger shaft has a plurality or longitudinally planar legs and wherein said control device is placed only between adjacent planar legs of said plunger shaft.

15. The device of claim 11 wherein said plunger shaft has a plurality or longitudinally planar legs and wherein said flute is placed only between adjacent planar legs of said plunger shaft.

* * * * *

UNITED STATES PATENT AND TRADEMARK OFFICE
CERTIFICATE OF CORRECTION

PATENT NO. : 5,000,737
DATED : March 19, 1991
INVENTOR(S) : Michael J. Free; Terence R. Ellard It is certified that error appears in the above-identified patent and that said Letters Patent is hereby corrected as shown below:

In column 5, claim 1, line 37, after "nozzle, said" please insert --plunger member comprising a plunger shaft extending --.

In column 6, claim 1, line 1, please delete "suppression" and substitute therefor --depression--.

In column 6, claim 4, line 19, please delete "forming" and substitute therefor --forcing--.

In column 6, claim 11, line 55, after "flute" please insert --being--.

In column 8, claim 14, line 2, please delete "or" and substitute therefor --of--.

In column 8, claim 15, line 6, please delete "or" and substitute therefor--of--.

Signed and Sealed this

First Day of September, 1992

Attest:

DOUGLAS B. COMER

Attesting Officer     Acting Commissioner of Patents and Trademarks